United States Patent [19]
Bycroft et al.

[11] Patent Number: 5,969,158
[45] Date of Patent: Oct. 19, 1999

[54] METHOD OF TREATING ALLERGIC DISEASE

[75] Inventors: Barrie Walsham Bycroft, Nottingham; Herbert Fitzgerald Sewell; Gordon Sydney Anderson Birnie Stewart, both of Leicester; Paul Williams, Nottingham, all of United Kingdom

[73] Assignee: The University of Nottingham, Nottingham, United Kingdom

[21] Appl. No.: 09/097,371

[22] Filed: Jun. 15, 1998

Related U.S. Application Data

[62] Division of application No. 08/569,257, filed as application No. PCT/GB94/01437, Jul. 1, 1994.

[30] Foreign Application Priority Data

Jul. 2, 1993 [EP] European Pat. Off. ............. 93305221

[51] Int. Cl.$^6$ ..................... C07D 333/36; C07D 305/12; A61K 31/38; A61K 31/34
[52] U.S. Cl. ........................... 549/63; 549/321; 514/445; 514/473
[58] Field of Search .................... 549/63, 321; 514/445, 514/473

[56] References Cited

U.S. PATENT DOCUMENTS

| | | | |
|---|---|---|---|
| 4,411,909 | 10/1983 | Gonella | 424/275 |
| 5,591,872 | 1/1997 | Pearson et al. | 549/321 |

FOREIGN PATENT DOCUMENTS

| | | |
|---|---|---|
| 061 386 | 9/1982 | European Pat. Off. . |
| 336 326 | 10/1989 | European Pat. Off. . |
| 25 13 842 | 10/1975 | Germany . |
| 1 506 934 | 4/1978 | United Kingdom . |
| 92/18614 | 10/1992 | WIPO . |

OTHER PUBLICATIONS

Chemical Abstracts, vol. 28, No. 7, Feb. 1973, Abstract No. 41213a.

Ljaljevic et al., Od. Med. Nauka, "New Views on the Mechanism of Allergic Reactions", vol. 24, pp. 137–143, 1971. (translation).

Chhabra et al., Journal of Antibiotics, vol. 46, No. 3, "Autoregulation of Carbapenem Biosynthesis in *Erwinia carotovora* by Analogues of N–(3–oxohexanoyl)–L–homoserine Lactone", pp. 441–454, Mar. 1993.

Marchioni et al., Lung, vol. 168, No. 5, "Effects of Erdosteine on Sputum Biochemical and Rheologic Properties: Pharmacokinetics in Chronic Obstructive Lung Disease", pp. 285–293, 1990.

Varga et al., Molecular Immunology, vol. 28, No. 6, "Mechanism of Allergic Cross–Reactions–1. Multispecific Binding of Ligands to A Mouse Monoclonal Anti–Dip IgE Antibody", pp. 641–654, 1991.

Cao et al., Journal of Bacteriology, vol. 175, No. 12, "Biosynthesis and Stereochemistry of the Autoinducer Controlling Luminescence of *Vibro harveyi*", pp. 3856–3862, Jun. 1993.

Papaccio, Diabetes Research and Clinical Practice, vol. 13, No. 1 & 2, "Prevention of Low Dose Streptozotocin–Induced Diabetes by Acetyl–Homocysteine–Thiolactone", pp. 95–102, 1991.

H. Kaplan et al., Chemical Abstract, 103:215746, searched by STN (1985).

A. Eberhard et al., Arch. Microbiol., 146: pp. 35–40 (Oct. 1986).

L. Zhang et al., Nature, 362: pp. 446–448 (Apr. 1993).

*Primary Examiner*—Deborah C. Lambkin
*Attorney, Agent, or Firm*—Wenderoth, Lind & Ponack, L.L.P.

[57] ABSTRACT

A compound having formula (1) for use as a medicament wherein n is 2 or 3; Y is O, S or NH; X is O, S or NH; and R is $C_1$–$C_{18}$ alkyl or acyl which may be substituted.

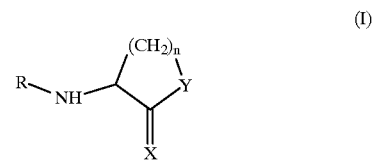

(I)

10 Claims, No Drawings

METHOD OF TREATING ALLERGIC DISEASE

This is a divisional of application Ser. No. 08/569,257 filed Feb. 5, 1996, U.S. Pat. No. 5,776,974, which was the national stage of International Application No. PCT/GB94/01437 filed Jul. 1, 1994.

FIELD OF THE INVENTION

This invention relates to compounds for use as medicaments and to pharmaceutical compositions containing these compounds.

DESCRIPTION OF RELATED ART

Responses by the immune system to inhaled proteins (allergens/antigens) underlie the clinical presentation of allergic rhinitis (e.g. hayfever) and asthma. Research in Immunology has established that the cross-linking of at least two IgE antibodies (these are naturally bound by their Fc portion to receptors on the surface of human leucocytes, namely blood basophils and tissue mast cells) sets into motion a series of biochemical and pharmacological events leading to the expression of clinical allergy. The cross-linking of surface bound IgE either by allergen or mimicked by using anti-IgE antibodies results in the release of potent mediators of inflammation which are stored or are synthesized within the granules of basophils and mast cells. The major inflammation inducing substance that is released is histamine, but more than twenty other molecules have been defined following the positive signal associated with cross-linking of IgE on the surface of these cells. Overall the release of these agents results in dramatic changes in smooth muscle, in the vasculature and in release of other chemotactic factors which attract other inflammatory cells (e.g. eosinophils, neutrophils). This leads to major synergism of these compounds and amplification of the inflammatory response which then manifests as clinical allergy, e.g., difficulty in breathing, itching, excess mucous secretion, etc. up to and including life-threatening generalized allergic reaction in some rare situations.

Therapeutically, many agents are used to try to prevent the release of mediators from mast cells and basophils and/or to treat the downstream events by blocking or ameliorating the effects of the mediators on target tissues. Therapeutic agents commonly employed fall under the following main groups:

1) Antihistamines—these are meant to block and mop up the released histamine, i.e. the major mediator of the allergic response.
2) β1, β2, agonist, e.g. Epinephrine, Salbutamol. These are meant to overcome indirectly the downstream effects on vasculature and smooth muscle.
3) Chromoglycate—this is useful for primary prevention of mast cells/basophil degranulation.
This prophylactic must be taken continuously. It does not prevent the cross-linking of IgE but it somehow interferes with subsequent events.
4) Theophylline and other phosphodiesterase inhibitors again influence downstream biochemical events particularly associated with cyclic nucleotides.
5) Steroids—these have multiple sites of activities against the allergic response. They are either administered locally and/or systematically.

None of these treatments is ideal and each has degrees of problems such as side effects and breakthroughs. Therefore, new agents are constantly being sought which may contribute to control of the allergic response prophylactically and/or therapeutically.

Immunosuppressant compounds induce an inhibition of the immune response system. Compounds which are known to exhibit immunosuppressant activity include the fungal metabolite Cyclosporin A and the macrolide antibiotic (a metabolite from *Streptomyces tsukabaensis*) termed FK506. Both of these agents have been used clinically and experimentally to suppress the immune system in transplantation and in the treatment of a number of diseases.

The immune mediated rejection process is the major cause of graft loss in organ transplantation. Dramatic improvements in immunosuppression (directed against proliferating T cells) and subsequent organ graft and patient survival have been obtained using Cyclosporin A. Encouraging results have also been obtained with FK506.

Autoimmune diseases are disorders where the host discrimination of "self" versus "non-self" breaks down and the individual's immune system (both acquired and innate components) attacks self tissues. These diseases range from extremely common entities such as rheumatoid arthritis, thyroid autoimmune disease and type 1 diabetes mellitus to less common entities such as multiple sclerosis and to rarer disorders such as myasthenia gravis. Advances in basic biomedical science and, in particular, in immunology have indicated that the main and fundamental lesion responsible for the induction and persistence of most autoimmune diseases resides within auto-reactive proliferating T lymphocytes. Both Cyclosporin A and FK506 have been used clinically in the treatment of autoimmune diseases with encouraging results.

Immunosuppressive agents, e.g., cyclosporin, have also been shown to control neoplastic cell proliferation in the treatment of T cell cancers.

The currently available immunosuppressant drugs have the disadvantage of a narrow therapeutic index, i.e., toxicity versus clinical benefit. The compounds are known to be nephrotoxic. neurotoxic and potentially diabetogenic and this has limited their use in the fields mentioned above. Problems also exist with the administration of these compounds, their bioavailability and the monitoring of their levels both clinically and in the laboratory.

SUMMARY OF THE INVENTION

We have now discovered a class of compounds which exhibits immunosuppressant activity and inhibits the release of histamine. These compounds, and methods for their preparation, are disclosed in WO-A-92/18614. However, this document only discloses that the compounds act as autoinducers and as agents for the control of gene expression in microorganisms and does not suggest that they have any pharmacological activity. Compounds in this series are also mentioned in *Journal of Bacteriology*, Volume 175, Number 12, June 1993, pages 3856 to 3862 but again there is no teaching that they might have any effect outside microorganisms.

G. Papaccio, *Diabetes Res. Clin. Pract.*, Vol 13, No. 1, 1991, pages 95–102 discloses the use of N-acetylhomocysteine thiolactone as an enhancer of superoxide dismutase in an attempt to increase protection against chemically induced diabetes.

The use of N-acetylhomocysteine thiolactone to modify the IgE molecule is taught by J. Ljaljevic et al in *Od. Med. Nauka*, Vol. 24, 1971, pages 137–143 and *Chemical Abstracts*, Vol. 78, No. 7, February 1973, abstract No. 41213a. However, there is no suggestion in this paper of immunosuppression or of the inhibition of histamine release.

In a first embodiment, the present invention provides a compound having the formula 1 for use as a medicament, wherein formula 1 is:

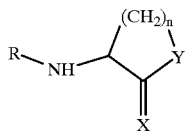

where: n is 2 or 3; Y is O, S or NH; X is O, S or NH; and R is $C_1$–$C_{18}$ alkyl or acyl which may be substituted. It is preferred that when n is 2, X is O and Y is S, R is not acetyl.

Preferably, Y is O or NH (more preferably O), X is O, n is 2 and R is acyl. It is also preferred that R carries a keto or hydroxy group, preferably in the beta-position. The compounds may be in the form of racemic mixtures, optically active isomers or mixtures thereof. It will be appreciated that the relatively small size of the compounds relative to those of the prior art means that they are likely to give rise to fewer potentially toxic metabolites.

The present invention also provides the use of the compounds of formula 1 in the manufacture of a medicament for the treatment of allergic diseases, such as asthma or hayfever, and/or autoimmune diseases. Methods of treatment of allergic diseases and/or autoimmune diseases comprising the administration to a patient of a compound of formula 1 are also provided by the invention.

In another embodiment, the invention provides a pharmaceutical composition comprising a compound of formula 1 and a pharmaceutically acceptable diluent or carrier. The appropriate diluent or carrier will depend on the method of administration of the composition and will be readily determinable by those skilled in the art.

The compounds of formula 1 significantly inhibit histamine release from human mast cells and/or basophils following cross-linking of the membrane-bound IgE molecules. Preferably, for histamine inhibiting activity, R is a $C_1$ to $C_{12}$ group. Compounds with both L- and D- stereochemistry at the ring carbon atom bound to the nitrogen atom have been found to be active, as inhibitors of histamine release and both L- and D-isomers of N-(3-oxohexanoyl) homoserine lactone have been shown to be effective. As a result of this activity, the compounds are expected to be useful in the treatment of disorders such as human clinical allergy. The benefits of a new class of compounds to treat this very common disorder are evident.

The compounds of the present invention have also been found to cause a marked inhibition of human lymphocyte reactivity (particularly T cell proliferative responses) and may be used as immuno-suppressors in any application where control of the human immune response system, particularly its inhibition, is important. For immunosuppressant activity, the compounds preferably contain R as a $C_7$–$C_{18}$ group and isomers which have L-stereochemistry at the ring carbon atom bound to the nitrogen atom are particularly preferred. Thus, like the existing immunosuppressants, the compounds and compositions of this invention may be used in vitro and in vivo, such as to prevent transplant rejection and in the treatment of autoimmune diseases (e.g., multiple sclerosis or rheumatoid arthritis). They may also be employed as controllers of T cell activation in the treatment of AIDS.

As a result of their activity in inhibiting T cell function, it is expected that the compounds and compositions of the invention will be of therapeutic value in the treatment of cancers associated with proliferating neoplastic T lymphocytes. Examples of this type of cancer include acute lymphoblastic leukaemias in adults and children, non-Hodgkins lymphomas, chronic lymphocytic leukemia and rarer diseases such as Hairy Cell Leukaemia and HTLVL associated T cell leukemia/lymphoma.

Other advantages of the compounds over the existing immunosuppressant agents can be seen to be derived from their structure and low molecular weight and include increased solubility in polar solvents, easier modes of administration, less intensive monitoring and significantly improved pharmacokinetics.

DETAILED DESCRIPTION OF THE PREFERRED EMBODIMENT(S)

EXAMPLES

Synthesis of [N-(3-oxohexanoyl)-L-homoserine lactone] and its analogues

1. Synthesis of N-(3-oxohexanoyl)-L-homoserine lactones
General Method

Triethylamine (1 mmol) was added to a stirred solution of homoserine lactone hydrochloride (the L- or D- isomer of a racemic mixture) (1 mmol) in water (2 ml) followed by the addition of ethylene glycol ketal of 3-oxoalkanoic acid (1 mmol) and 1-ethyl-3-(3-dimethylaminopropyl)carbodiimide hydrochloride (1 mmol). The mixture was stirred for 20 h and then rotary evaporated to dryness at about 35° C. The light orange residue was extracted with warm ethyl acetate (5×5 ml), and the extracts pooled and washed successively with water (1×3 ml), 5% sodium bicarbonate solution (1×3 ml), 1 M potassium hydrogen sulphate solution (1×3 ml) and finally brine (1×5 ml). Drying ($MgSO_4$) and evaporation of solvent in vacuo gave the ethylene glycol ketal of 3-oxoalkanoylated homoserine lactones (40–50%).

Perchloric acid (60%, 0.25 ml) was added to an ice-cooled solution of the alkanoylated lactone (0.5 mmol) in dichloromethane (15 ml). The mixture was stirred at 0° C. for 0.5 h and then at room temperature for 1.5 h. The solvent was removed in vacuo and the residue redissolved in ethyl acetate (20 ml). The solution was washed with cold water (2×5 ml) and brine (1×5 ml), dried ($MgSO_4$) and rotary evaporated to obtain the desired N-(3-oxoalkanoyl) homoserine lactones (55–60%).

2. Synthesis of N-acylated homoserine lactone
General Method

Triethylamine (1 mmol) was added to a stirred solution of homoserine lactone hydrochloride (the L- or D- isomer or a racemic mixture) (1 mmol) in water (2 ml) followed either by the addition of acid anhydride (3 mmol) or acid (1.5 mmol) and 1-ethyl-3-(3-dimethylaminopropyl)carbodiimide hydrochloride (1.5 mmol). The mixture was stirred at room temperature overnight and then evaporated in vacuo to dryness. The residue was partitioned between water (5 ml) and ethyl acetate (20 ml) and the organic layer successively washed with 5% $NaHCO_3$ solution (2×5 ml), 1 M $KHSO_4$ solution (1×5 ml) and brine (1×5 ml). Drying ($MgSO_4$) and removal of solvent gave the title acylated lactones (20–60%)

3. Synthesis of N-(3-hydroxyalkanoyl)-L-homoserine lactones
General Method

N-(3-Oxoalkanoyl)-L-homoserine lactone (0.2 mmol) was dissolved in methanol (5 ml) and the solution made acidic (pH 3–4) with 2 M HCl-methanol. Sodium cyanoborohydride (0.5 mmol) was added in one lot with stirring and the reaction mixture maintained at pH 3–4 by the occasional addition of 2 M HCl-methanol,. After 2 h, solvent was removed in vacuo and ethyl acetate extracts (3×5 ml) of the residue were combined, dried ($MgSO_4$) and evaporated to yield the title hydroxy derivatives. The products were purified by preparative layer chromatography on silica plates in CHCl$_3$—MeOH (9:1) and repurified by HPLC. The latter may be resolved and the diastereoisomers separated.

The compounds prepared by these methods were more than 90% pure and were further purified with reverse phase HPLC using a 1×25 cm S50DS2 semi-prep column eluting isocratically with 15–20% MeOH—H$_2$O mixture and monitoring at 210 nm. The products were freeze-dried and stored below 0° C.

EXAMPLE 1
Inhibition of Histamine Release

The D- and L-isomers of N-(3-oxohexanoyl) homoserine lactone (OHHL) were used in studying the inhibition of histamine release by the compounds of formula 1. OHHL has the following structural formula:

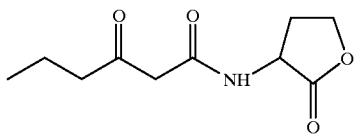

In order to quantify histamine release, the following were used:
Pharmacia TM Methyl Histamine Radioimmunoassay (RIA) Code No. 10-9138-01
Pharmacia TM Histamine Standard Code No. 10-9206-01
Assay Principle Anti-IgE cross-links receptor bound IgE on basophil cell surface. Histamine is released into the plasma. The histamine contained in the plasma competes with a fixed amount of $^{125}$I labelled histamine-albumin complex (CSA) for a monoclonal anti-histamine antibody. Antibody bound material is separated by the addition of a second antibody and immunoadsorbent, which can be centrifuged and unbound material decanted away.

Compounds (D-isomer and L-isomer) were dissolved in dimethyl sulphoxide (DMSO) initially, and subsequently diluted in Pipes-Ca buffer:

| Pipes-Ca Buffer pH 7.4 | |
|---|---|
| Pipes (Piperazine-N,N'-bis [2-ethanesulfonic acid] | 3.02 g/l |
| sodium acetate - trihydrate | 19.05 g/l |
| Potassium Acetate | 0.49 g/l |
| Human Serum Albumin | 0.30 g/l |
| Glucose | 1.00 g/l |
| Calcium Chloride - dihydrate | 0.15 g/l |
| Buffered to pH 7.4 with 1 M Tris Buffer. | |

Theophylline was reconstituted directly in Pipes-Ca buffer. The anti-IgE preparation is E1, a mouse monoclonal anti-human IgE, diluted in Pipes-Ca buffer. E1 is used at a standard concentration in this assay at 1:40 000 of a 1 mg/ml stock solution. Blood was donated by an atopic male individual.

Whole blood was collected by venipuncture, using heparin as an anti-coagulant, and fresh blood collected the same day was used in each experiment. 200 µl of whole blood was incubated with 190 µl of compound in DMSO/Pipes-Ca buffer for 30 minutes at 37° C., with gentle shaking every 10' minutes then 10 µl of anti-IgE added and the resulting assay mixture incubated for a further 60 minutes at 37° C. with gentle shaking every 10 minutes.

The assay is stopped by placing the tubes in an iced water bath (for a maximum of 10 minutes) and the samples centrifuged at 700 g for 10 minutes at 4° C. 200 µl of supernatant is extracted for the histamine assay, then 200 µl $^{125}$I-histamine CSA and 200 µl anti-histamine antibody is added to all tubes.

A standard curve of histamine is produced by diluting the histamine standard. The standard histamine tubes are treated in exactly the same manner as the assay tubes, i.e. $^{125}$I-histamine and the anti-histamine antibody added to the standard histamine tubes as well.

These components are incubated for 16 hours at 4° C. after which 2 ml of decanting suspension (provided in Pharmacia ™kit) is added to each tube and the mixture is incubated for 30 minutes at room temperature and centrifuged for 10 minutes at 1500 g at room temperature. The supernatant is decanted off and the tubes counted in a gamma counter with $^{125}$I detection facilities. All gamma counter results are expressed as a percentage of the mean counts of that of the diluent (i.e. containing no histamine) [% activity bound].

Once the counts have been represented as % activity bound, they can be quantified by obtaining the concentration of histamine this represents from the standard curve.

The results are subsequently corrected for spontaneous (background) release and then expressed as percentage of total release.

Total histamine release is achieved by three freeze thaw cycles, or sonication using a probe (not a sonicating bath). 200 µl of whole blood is mixed with 800 µl of water, to ensure the histamine value will fall within the standard curve range (when calculating results, correct for this by multiplying the 'Totals' result by a factor of 2.5).

Spontaneous—Background histamine release levels —produced by incubating whole blood with the Pipes-Ca for the assay period—in this case 90 minutes at 37° C.

Initially, two isomers, the D-isomer and L-isomer of OHHL were tested at three doses. The final concentrations used in the histamine release assay, measured in whole blood were 241 µg/ml, 24 µg/ml and 2.4 µg/ml. The final concentration of DMSO used in the experiment was 2% and this factor was controlled for.

It was found that DMSO controls of 2.0%, 1.0% and 0.1% did not cause any significant histamine release.

The isomers were themselves tested in the assay without the presence of the anti-IgE, and it was found that the compounds alone did not cause significant histamine release.

The anti-IgE used in the assay to induce histamine release was a murine monoclonal anti-IgE with an epitope specificity directed against a region located in the Cє4 domain of IgE.

Both the D-isomer and L-isomer inhibited the anti-IgE induced histamine release. A 43.5% inhibition of the anti-IgE release was observed with the D-isomer when used in the assay at 241 µg/ml, and 55.3% inhibition of the anti-IgE release was achieved with the L-isomer when used at the same concentration. It was found that the subsequent concentrations tested did not cause any inhibition of anti-IgE induced histamine release, and therefore this inhibition of anti-IgE induced histamine release was not found to be dose dependent over the range of concentrations tested.

The experiment was repeated, using a different range of concentrations, in order to establish dose dependency. The concentrations tested were 241 µg/ml, 48 µg/ml and 24 µg/ml. The two isomers were both found to modulate the anti-IgE induced histamine release in a dose dependent manner. The L-isomer inhibited the anti-IgE induced histamine release by 62.5% when assayed at a concentration of 241 μg/ml. The D-isomer inhibited the anti-IgE induced histamine release by 45.9% when tested at a final concentration of 241 μg/ml. Inhibition of the anti-IgE induced histamine release was observed at a concentration of 48 μg/ml but not at 24 μg/ml showing that the response was noticeably dose dependent.

Theophylline (a non-selective phosphodiesterase inhibitor) was used in the assay at two concentrations $10^{-3}M$ and $10^{-7}M$, as a standard inhibitor of histamine release. It was assayed in conjunction with the same concentration of anti-IgE used throughout the experiment. Dose dependent inhibition of anti-IgE induced histamine release was observed with the two concentrations of theophylline tested. At the top concentration of theophylline ($10^{-3}M$) a 67.1% inhibition of anti-IgE induced histamine was observed.

Reproducible inhibition of anti-IgE induced histamine release was achieved with both the D-isomer and the L-isomer.

EXAMPLE 2
Immunosuppression

The methods and materials used in the analysis of immunosuppressive effects were based on the techniques disclosed in H Chapel and H F Sewell, Cellular immune deficiency: cell assays for special immune deficiency; Chapter 2 in: *Clinical Immunology—A Practical Approach*: Ed. H M Chapel and H. C. Gooi, IRL—Oxford University Press, published 1990; and J. Woo, H. F. Sewell and A. W. Thomson (1990) The influence of FK506 and low concentration cyclosporin on human lymphocyte activation antigen expression and blastogenesis: A flow cytometric analysis. *Scan. J. Immunol.*, 31, 297.

Purified N-(3-oxododecanoyl)-L-homoserine lactone was dissolved in DMSO and diluted with aqueous buffer at pH6.

Peripheral blood mononuclear cells (PBMC) were prepared by isolation using standard ficoll hypaque procedures from venous blood collected from healthy donors.

(a) Concanavalin A Lymphocyte Transformation Assay

Concanavalin A was used at a final concentration of 2.5 μg/ml.

PBMC at $5 \times 10^5$ ml in RPMI (Roche Park Memorial Institute) +10% AB serum were incubated with Concanavalin A. Cultures were established with and without the addition of N-(3-oxododecanoyl)-L-homoserine lactone at a final concentration of 0.5, 5 and 25 μg/ml. Cultures were also established with corresponding amounts of DMSO only as controls.

Cells were cultured at 37° C. with 5% carbon dioxide in air mixtures for 72 hours.

Labelling and harvesting of cells was performed by the addition 20 μl (0.2 μCi) of [$^3$H] thymidine (Amersham) and incubated for 20 hours. The cells were harvested onto glass fibre discs and the amount of thymidine uptake was measured using a liquid scintillation counter.

Mean counts per minute (cpm) were determined.

The results are shown in Table 1.

TABLE 1

|  | CPM |
|---|---|
| Concanavalin A (2.5 μg/ml in RPMI) | 2699 |
| Concanavalin A (2.5 μg/ml in DMSO) | 47.03 |
| Lactone (25 μg/ml) in 5% DMSO | 38.13 |
| Lactone (5 μg/ml) in 1% DMSO | 187.05 |

TABLE 1-continued

|  | CPM |
|---|---|
| Lactone (0.5 mg/ml) in 0.1% DMSO | 2103.73 |
| DMSO only (5%) | 33.28 |
| DMSO only (1%) | 685.88 |
| DMSO only (0.1%) | 1849.15 |

The results show that at 5 μg/ml in 1% DMSO, the compound exhibits immunosuppression. At a concentration of 5%, DMSO clearly blocks Concanavalin A stimulation of lymphocytes and the result for the compound at a concentration of 25 μg/ml is. therefore, uninterpretable.

A number of members of the class of compounds of formula 1, both D and L isomers, are shown in WO-A-92/18614 to control gene expression in microorganisms. In view of this fact, it is reasonable to infer from results we have obtained that these compounds will also show inhibition of histamine release and/or immunosuppressant activity. Compounds disclosed in WO-A-92/18164 as controlling gene expression and, therefore, expected to act as inhibitors of histamine release and/or immunosuppressors include the following:

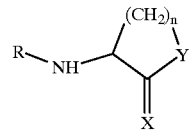

| R | Y | Chirality at C-3 |
|---|---|---|
| CH₃CH₂CH₂COCH₂CO | O | L (OHHL) |
| CH₃CH₂CH₂COCH₂CO | O | D |
| CH₃CH₂COCH₂CO | O | L |
| CH₃CH₂CH₂CO | O | L |
| CH₃CH₂CH₂CH=CHCO | O | L |
| (RS)—CH₃CH₂CH(OH)CH₂CO | O | L |
| CH₃CH₂CH₂CH₂COCH₂CO | O |  |
| CH₃CH₂CH₂COCH₂CO | S |  |
| CH₃CH₂CH₂CH₂CH₂CO | O | L |
| (S)—CH₃CH₂CH(OH)CH₂CO | O | L |
| (R)—CH₃CH₂CH₂CH(OH)CH₂CO | O | L |
| PhCOCH₂CO | O | L |

We claim:

1. A method of treating an allergic disease, comprising administering to a patient in need thereof an effective amount of a compound having the following formula:

wherein n is 2, Y is O or S; X is O, S or NH; and R is $C_1$–$C_{18}$ alkyl or acyl which may be substituted, provided that when Y is S and X is O, R is not acetyl.

2. A method as claimed in claim 1, wherein Y is O, X is O and R is acyl.

3. A method as claimed in claim 1, wherein R contains a keto or a hydroxy group.

4. A method as claimed in claim 3, wherein R contains a keto group in the beta-position.

5. A method as claimed in claim 1, wherein the compound has L stereochemistry at the ring carbon atom bound to the nitrogen atom.

6. A method as claimed in claim 1, wherein R is a $C_1$–$C_{12}$ group.

7. A method as claimed in claim 1, wherein the compound is N-(3-oxohexanoyl)homoserine lactone.

8. A method as claimed in claim 1, wherein the compound is N-(3-oxododecanoyl)homoserine lactone.

9. A method as claimed in claim 1, wherein the allergic disease is asthma or hay fever.

10. A method for inhibiting histamine release from mast cells and/or basophils, comprising administering to a patient in need thereof an effective amount of a compound having the following formula:

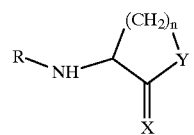

wherein n is 2; Y is O or S; X is O, S or NH; and R is $C_1$–$C_{18}$ alkyl or acyl which may be substituted, provided that when Y is S and X is O, R is not acetyl.

* * * * *